(12) United States Patent
Haddadi et al.

(10) Patent No.: US 8,916,205 B2
(45) Date of Patent: Dec. 23, 2014

(54) POLYMERIC NANOPARTICLES FOR PHOTOSENSITIZERS

(75) Inventors: Azita Haddadi, Saskatoon (CA); Ragupathy Madiyalakan, Edmonton (CA); Thomas Woo, Edmonton (CA)

(73) Assignee: Quest Pharmatech Inc., Edmonton (CA)

( * ) Notice: Subject to any disclaimer, the term of this patent is extended or adjusted under 35 U.S.C. 154(b) by 0 days.

(21) Appl. No.: 14/236,212

(22) PCT Filed: Aug. 11, 2011

(86) PCT No.: PCT/CA2011/000916
§ 371 (c)(1),
(2), (4) Date: Jan. 30, 2014

(87) PCT Pub. No.: WO2013/020204
PCT Pub. Date: Feb. 14, 2013

(65) Prior Publication Data
US 2014/0170229 A1    Jun. 19, 2014

(51) Int. Cl.
| | | |
|---|---|---|
| A61K 9/14 | (2006.01) | |
| C07C 49/84 | (2006.01) | |
| A61K 41/00 | (2006.01) | |
| A61K 9/06 | (2006.01) | |
| A61K 9/00 | (2006.01) | |
| A61K 9/51 | (2006.01) | |

(52) U.S. Cl.
CPC ............. A61K 41/0057 (2013.01); C07C 49/84 (2013.01); A61K 9/06 (2013.01); A61K 9/0019 (2013.01); A61K 9/5153 (2013.01); A61K 9/0014 (2013.01); Y10S 977/773 (2013.01)
USPC .......................................... 424/489; 977/773

(58) Field of Classification Search
CPC ................ A61K 41/0057; A61B 2017/22087; A61N 5/062
See application file for complete search history.

(56) References Cited

U.S. PATENT DOCUMENTS

2010/0262115 A1* 10/2010 Madiyalakan et al. ........ 604/500

OTHER PUBLICATIONS

YN Konan, M Berton, R Gurny, E Allemann. "Enhanced photodynamic activity of meso-tetra(4-hydroxyphenyl)porphyrin by incorporation into sub-200 nm nanoparticles." Euroepan Journal of Pharmaceutical Sciences, vol. 18, 2003, pp. 241-249.*
D Bechet, P Couleaud, C Frochot, ML Viriot, F Guillemin, M Barberi-Heyob. "Nanoparticles as vehicles for delivery of photodynamic therapy agents." Trends in Biotechnology, vol. 26 No. 11, 2008, pp. 612-621.*
A Budhian, SJ Siegel, KI Winey. "Production of haloperidol-loaded PLGA nanoparticles for extended controlled drug release of haloperidol." Journal of Microencapsulation, vol. 22(7), Nov. 2005, pp. 773-785.*
M Korbelik, S Merchant, N Huang. "Explotation of Immune Response-eliciting Properties of Hypocrellin Photosensitizer SL052-based Photodynamic Therapy for Eradication of Malignant Tumors." Photochemistry and Photobiology, vol. 85, 2009, pp. 1418-1424.*
BT Paul, MS Babu, TR Santhoshkumar, D Karunagaran, GS Selvam, K Brown, T Woo, S Sharma, S Naicker, R Murugesan. "Biophysical evaluation of two red-shifted hypocrellin B derivatives as novel PDT agents." Journal of Photochemistry and Photobiology B: Biology, vol. 94, 2009, pp. 38-44.*
Allemann et al. In vitro extended-release properties of drug-loaded Poly (Dl-Lactic Acid) Nanoparticles Produced by slating-Out Procedure, Pharnaceutical Research, vol. 10 , No. 12, 1993 173-191.
Allen et al."Photodynamic therapy: Targeting cancer cells with photosensitizer-bioconjugates" in "Cancer Drug Discovery and Development: Tumor Targeting in Cancer Therapy"(M. Pagé ed.,Humana Press),2002, Chapter18, pp. 329-361.
Alshamsan et al. "STAT3 Silencing in Dendritic Cells by siRNA Polyplexes Encapsulated in PLGA Nanoparticles for the Modulation of Anticancer Immune Response" ;vol. 7, No. 5, 1643-1654 Molecular Pharmaceutics; 2010.
Bechet et al."Nanoparticles as vehicles for delivery of photodynamic therapy agents",France,Trends in Biotechnology vol. 26 No. 11, 10 pages, Sep. 17, 2008.
Chatterjee et al."Nanoparticles in photodynamic therapy; An emerging paradigm" Advanced Drug delivery reviews, 2008, 60, 1627-1637.
Das et al. "Delivery of rapamycin-loaded nanoparticle down regulates ICAM-1 expression and maintains an immunosuppressive profile in human CD34 Þ progenitor-derived dendritic cells" 2007 Wiley Periodicals, Inc., 10 pages.
Diwu et al. Phototherapeutic potential of alternativ photosensitizers to porphyrins Pharmac.Ther.vol. 63,pp. 1-35, 1994.
Ghotbi et al. "Active targeting of dendritic cells with mannan-decorated PLGA nanoparticles" Journal of Drug Targeting, 2011; 19(4): 281-292.
Haddadi et al. "Delivery of rapamycin by PLGA nanoparticles enhances its suppressive activity on dendritic cells" Journal of Biomedical Materials Research Part A, 2007, 14 pages.
Haddadi et al. "Preparation and characterization of biodegradable urea-loaded microparticles as an approach for transdermal delivery" Journal of Microencapsulation, Sep. 2006; 23(6): 698-712.
Haddadi et al. "Topical delivery of urea encapsulated in biodegradable PLGA microparticles: O/W and W/O creams"; Journal of Microencapsulation, Sep. 2008; 25(6): 379-386.
Hamdy et al. "Activation of Antigen-Specific T Cell-Responses by Mannan-Decorated PLGA Nanoparticles" Pharm Res (2011) 28:2288-2301.

(Continued)

*Primary Examiner* — Frederick Krass
*Assistant Examiner* — Isaac Shomer
(74) *Attorney, Agent, or Firm* — Benoit & Cote Inc.

(57) ABSTRACT

Biodegradable polymeric nanoparticles comprising an inner core formed of a photodynamic agent capable of being activated to generate cytotoxic singlet oxygen are prepared. These nanoparticles have anti-cell proliferation activity and are useful in treating both cancerous and non-cancerous conditions including actinic keratosis, psoriasis and acne vulgaris. Preferably, the photodynamic agent is a hypocrellin B derivative while the polymeric nanoparticle comprises polyglycolic acid, polylactic acid or poly(lactide-co-glycolide). Hypocrellin-comprising nanoparticles are demonstrated to be activated by light or hydrogen peroxide.

5 Claims, 11 Drawing Sheets

(56) References Cited

OTHER PUBLICATIONS

Hamdy et al. "Part I: Targeted Particles for Cancer Immunotherapy" Current Drug Delivery, 2011, 8, 261-273.

Hamdy et al. "Pharmaceutical analysis of synthetic lipid A-based vaccine adjuvants in poly (d,l-lactic-co-glycolic acid) nanoparticle formulations" Journal of Pharmaceutical and Biomedical Analysis 44 (2007) 914-923.

Hamdy et al. "Co-delivery of cancer-associated antigen and Toll-like receptor 4 ligand in PLGA nanoparticles induces potent CD8+ T cell-mediated anti-tumor immunity" Vaccine 26 (2008) 5046-5057.

Hamdy et al. "Targeting dendritic cells with nano-particulate PLGA cancer vaccine formulations" Advanced Drug Delivery Reviews 63 (2011) 943-955.

Hung et al. "Targeted Particles for Imaging of Anticancer Immune Responses" Current Drug Delivery, 2011, 8, 000-000, 2011 Bentham Science Publishers Ltd.

Korbelik et al. "Antitumor Efficacy of Photodynamic Therapy Using Novel Nanoformulations of Hypocrellin Photosensitizer SL052" Photochemistry and Photobiology, 2012, 88: 188-193.

Meng et al. "Water-soluble and biocompatible sono/photosensitizer nanoparticles for enhanced cancer therapy" Nanomedicine (2010) 5(10). 1559-1569.

Pagonis et al. "Nanoparticle-based Endodontic Antimicrobial Photodynamic Therapy" JOE—vol. 36, No. 2, Feb. 2010.

Sharman et al. "Photodynamic therapeutics: basic principles and clinical applications" Drug Discovery Today, 1999, 4(11), 507-517.

Sharman et al. "Role of activated oxygen species in photodynamic therapy" Methods in Enzymology, 2000, 319, 376-400.

Yong-Eun Koo Lee et al. "polymeric nanoparticles for photodynamic therapy", Biomedical Nanotechnology; Methods and Protocoals, Methods in Molecular Biology, vol. 726, year is 2011.

Zeisser-Lalouebe et al. "Hypericin-loaded nanoparticles for the photodynamic treatment of ovarian cancer"; International Journal of Pharmaceutics 326 (2006) 174-181.

Zhao et al. "A novel water-soluble nanoparticles of hypocrellin B and their interaction with a model protein: C-phycocyanin"; Biochimica et Biophysica Acta 1670 (2004) 113-120.

PCT/International Search Report (ISR)—PCT/CA2011/000916 (Form PCT/ISA/210)—May 10, 2012—7 pages.

* cited by examiner

Bright Field

Epifluorescence

H&E (5-7μm section)

POLYMERIC NANOPARTICLES FOR PHOTOSENSITIZERS

CROSS REFERENCE TO RELATED APPLICATIONS

This application is a US National Phase application under 35 USC §371 of PCT/CA2011/000916, filed Aug. 11, 2011, the specification of which is hereby incorporated by reference in its entirety.

TECHNICAL FIELD

The present invention relates to polymeric nanoparticles, pharmaceutical compositions comprising same, and methods for using same for compound delivery to target tissue. More specifically, the present invention relates to polymeric nanoparticles, pharmaceutical compositions comprising same, and methods for using same, wherein the nanoparticles are taken up by target tissue and are capable of being activated to generate cytotoxic levels of singlet oxygen.

BACKGROUND

Photodynamic therapy (PDT) is well known, having clinical applicability in both cancerous and non-cancerous indications. PDT involves a compound known as a "photosensitizer" which can be excited or activated in a variety of ways, including, for example, by visible or near infrared light of a specific wavelength. PDT treatment is an oxygen dependent reaction, in which the production of reactive oxygen species causes tissue damage by cellular necrosis or apoptosis. Indeed, the availability and/or generation of oxygen can influence the success of PDT.

PDT treatment involves administering a photosensitizing agent to a patient for delivery of the agent to a target tissue, illuminating the target tissue and activating the photosensitizer, which acts as a catalyst to destroy the target tissue by generating singlet oxygen. Like most catalysts, photosensitizers are not themselves destroyed during the activation process, and can thus be used repeatedly with proper activation.

PDT has become known as an effective treatment modality for various types of cancer including, lung cancer, head and neck cancer, bladder cancer, Barrett's oesophagus, and skin cancer. Non-cancerous applications include degenerative eye disorders, such as, macular degeneration, skin conditions such as, actinic keratosis, psoriasis, localized scleroderma, acne vulgaris and granuloma annulare, and inflammatory (rheumatoid arthritis) and infective disorders (e.g. dental infections, Leishmaniasis).

Research has shown that PDT for cancer provides numerous advantages over conventional therapies, such as chemotherapy and radiation, including higher efficacy with localized and specific tumour treatments, and potential for repetition of therapy without cumulative toxicity. PDT, which can be an outpatient therapy, also reduces the duration of treatment when compared to the weeks to months of radiotherapy, chemotherapy and/or prolonged hospitalization after surgery. Finally, in contrast to most conventional cancer therapies, PDT can induce immunity and thus may contribute to long-term control of abnormal cell proliferation.

Due to their high lipophilicity, delivery of photosensitizers for clinical applications can be problematic. In an attempt to overcome this challenge, various encapsulation strategies have been studied to protect the hydrophobic photosensitizer from aqueous environments.

Once such strategy involves the use of non-biodegradable nanoparticles for the delivery of photosensitizer compounds such as, ceramic (silica), gold, iron oxide and polyacrylamide nanoparticles. Such nanoparticles are not typically utilized as a means of compound delivery due to their inability to degrade and to release compounds in a controlled manner. However, given that photosensitizers are not themselves toxic to targeted cells, but instead act like catalysts to produce toxic products from non-toxic dissolved oxygen, non-biodegradable nanoparticles may be used as carriers for directed delivery of photosensitizers to target tissue. To be effective, however, non-biodegradable nanoparticles must be small enough in size to have a volume of distribution roughly equivalent to that of the photosensitizer, thereby extensively limiting compound size to a maximum allowable diameter of 100 nm, and preferably less than 50 nm.

Another strategy involves the use of biodegradable nanoparticles, which are advantageously capable of providing high compound loading, the possibility of controlling compound release and the existence of a wide variety of materials and manufacturing processes. Biodegradable nanoparticles are solid colloidal particles formed by the association of suitable polymers. It is known that the chemical composition of such polymers can be readily designed to incorporate compounds with variable degrees of hydrophobicity, molecular weight and charge. The surface properties and morphologies can also be optimized for controlled compound release kinetics and polymer degradation. For instance, attachment of site-specific moieties may enable active targeting of compounds, and modifying the surface with polymers, such as poly(ethylene glycol) and poly(ethylene oxide) may prolong circulation times. As such, biodegradable nanoparticles are known as pharmaceutically acceptable delivery vehicles for lipophilic compounds, such as, for example, photosensitizers.

Due to difficulties in applying light therapy, including the costs of the light source and variability of light application by people in their home, PDT treatment can also suffer from inadequate or inconsistent activation of photosensitizers, thereby reducing the efficacy of the clinical application. Given the essential role of oxygen in PDT therapy, it may be possible to use alternative activation methods of photosensitizers and/or oxygen production to enhance PDT treatment. For instance, increasing the availability of oxygen by, for example, the application of hydrogen peroxide may provide a synergistic effect when applied in combination with PDT treatment.

Thus, there is first a need for a compound (e.g., photosensitizer) delivery system that can incorporate the compound within the system efficiently without loss or alteration of its activity, be biodegradable and result in minimum immunogenicity. The system may further provide a selective accumulation (i.e. in therapeutic concentrations) of the compound within the diseased tissue with little or no uptake by normal/healthy surrounding cells. The system may further provide an environment for the compound to be administered parenterally (systemically or topically or in aerosol suspension) for treatment. There is also a need for a means for activating a compound (e.g. photosensitizer) that may or may not involve the use of light.

SUMMARY

A nanoparticle incorporating a photosensitizer capable of being activated to generating singlet oxygen is provided. More specifically, a nanoparticle comprising a biodegradable polymer-encapsulated inner core incorporating a photosensitizer capable of being activated to generate singlet oxygen is provided. The present nanoparticle may comprise a biodegradable polymer comprising polyglycolic acid, polylactic acid or a poly(lactide-co-glycolide). In one embodiment, the biodegradable polymer may comprise a poly(lactic-co-glycolic acid) or "PLGA" polymer, or the like.

The present nanoparticle may further comprise a photosensitizer formed of hypocrellin B, or a derivative thereof. The present nanoparticle may be capable of being activated by photodynamic therapy (PDT) treatment (e.g. light), hydrogen peroxide, the combination thereof, and/or any other means of activating the generation singlet oxygen at a target tissue.

In one aspect, the present nanoparticle may be capable of anti-cell proliferation activity such as, for example, cancerous (e.g. anti-tumour activity) and/or non-cancerous (e.g. hair removal) activity.

In one aspect, a pharmaceutical composition capable of anti-cell proliferation activity comprising the present biodegradable nanoparticle, in combination with one or more pharmaceutically acceptable carriers, is provided.

In another aspect, a method for using the present biodegradable nanoparticle, and/or pharmaceutical composition comprising same, incorporating a photosensitizer capable of being activated to generate singlet oxygen at a target tissue is provided, the method comprising:
  providing the present nanoparticles and/or pharmaceutical composition comprising same, wherein the nanoparticles and/or composition are capable of being internalized by the tissue,
  contacting target tissue with the present nanoparticle and/or pharmaceutical composition, and
  activating the present nanoparticle and/or pharmaceutical composition to generate cytotoxic singlet oxygen upon exposure of activation means.

In one aspect, the means of activation may comprise light and/or hydrogen peroxide. In another aspect, contacting the target tissue may be parenterally (e.g. systemically and/or topically).

In another aspect, a method of manufacturing a pharmaceutical composition capable of being activated to generate cytotoxic levels of singlet oxygen at a target tissue is provided, wherein the composition comprises the present nanoparticle.

In another aspect, a method for delivering a photosensitizing compound capable of being activated to generate cytotoxic levels of singlet oxygen at a target tissue, the method comprising:
  providing a biodegradable polymeric nanoparticle comprising an inner core formed of hypocrellin B, or a derivative thereof,
  contacting the target tissue with an effective amount of the nanoparticle,
  wherein the nanoparticle is internalized by the tissue to release the hypocrellin B, or derivative thereof, upon activation.

DESCRIPTION OF THE EMBODIMENTS

The invention will now be described by way of exemplary embodiments with reference to the attached FIGS. 1-11 and Table 1.

A nanoparticle incorporating a photosensitizer capable of being activated to generate singlet oxygen for anti-cell proliferation activity, whether normal or abnormal cell proliferation activity (e.g. anti-tumour, hair removal, etc) is provided. The present nanoparticle may be activated by photodynamic therapy (PDT) treatment and/or hydrogen peroxide.

The present nanoparticle may comprise any known biodegradable polymer. Preferably, the present nanoparticle may be comprised of poly(lactic-co-glycolic acid) or "PLGA". PLGA is commercially available in two forms based upon the functionality of its end groups, namely, ester-terminated or free carboxylic acid (COOH)-terminated. Each form of PLGA polymer is available in a wide range of molecular weights and ratios of lactic/glycolic acid, and has many advantages including, biocompatibility with a wide range of compounds and/or drugs, suitable biodegradation kinetics and physicochemical properties and ease of processing. The PLGA polymer has been widely used to prepare various biodegradable compounds including microparticles and nanoparticles. PLGA-nanoparticles have been investigated for sustained and targeted/localized delivery of different compounds including drugs, peptides, proteins and plasmid DNA.

Indeed, numerous studies have been done to characterize the applicability of PLGA-nanoparticles for use in the targeted delivery of photosensitizers, including, zinc (II) phthalocyanine encapsulated PLGA-nanoparticles for improving photodynamic activity in a target tissue, meso-tetra (carboxyphenyl) porphyrin (TCPP) nanoparticles for inducing tumour-inhibiting efficacy, bateriochlorophyll-a (BChl-a) loaded PLGA-nanoparticles for providing higher efficiency in singlet oxygen production, and PLGA-nanoparticles provide increased Indocyanine green (ICG) concentration and circulation time in plasma as well as ICG uptake, accumulation and retention in various organs.

The present disclosure relates to the applicability of PLGA-nanoparticles for use in the delivery of photosensitizers having anti-cell proliferation activity. For instance, hypocrellin B is a perylenequinone pigment isolated from the parasitic fungus *Hypocrella bambusae*, and has traditionally been used as a Chinese medicine to treat rheumatoid arthritis, gastric diseases, and skin diseases related to fungal infections. Hypocrellins exhibit potential activation by ultrasound as sonosensitizers as well as photosensitizer compounds based upon their photodynamic properties and their ability to generate singlet oxygen. As such, a suitable photosensitizer for incorporation into the present invention may comprise a hypocrellin B (see FIG. 1), or derivatives thereof.

A polymeric PLGA-nanoparticle encapsulating a photodynamic therapy agent or photosensitizer and capable of being activated to produce singlet oxygen is provided. In one embodiment, the present PLGA-nanoparticle may comprise a poly(lactic-co-glycolic acid) polymer having an ester-terminus and may encapsulate a photodynamic therapy agent or photosensitizer. In another embodiment, the present PLGA-nanoparticle may comprise a poly(lactic-co-glycolic acid) polymer having a free carboxylic acid (COOH)-terminus and may encapsulate a photodynamic therapy agent or photosensitizer.

A polymeric PLGA-nanoparticle encapsulating a photodynamic therapy agent or photosensitizer and capable of being activated to produce singlet oxygen is provided. The present PLGA-nanoparticle may comprise a poly(lactic-co-glycolic acid) polymer having an ester-terminus or having a free carboxylic acid (COOH)-terminus. The present PLGA-nanoparticle may encapsulate an inner core comprising hypocrellin B, or a derivative thereof. In one embodiment, the inner core may comprise hypocrellin B, or a derivative thereof, having the structure defined in FIG. 2, hereinafter referred to as "SL052". In another embodiment, the present PLGA-nanoparticle may encapsulate an inner core comprising hypocrellin B, or a derivative thereof, having the structure defined in FIG. 3, hereinafter referred to as "SL017".

In one aspect, the present PLGA-nanoparticles may be directed to a pharmaceutical composition having anti-cell proliferation activity comprising the present biodegradable nanoparticle, in combination with one or more pharmaceutically acceptable carriers. A person having skill in the art would know and understand that any pharmaceutically acceptable carrier that would be useful in this regard would be applicable, and therefore the procedure for making pharmaceutical compositions in accordance with the present embodiments would also be applicable. The pharmaceutical compositions may be in the form of tablets, capsules, liquids, lozenges, lotions, aerosol, and solutions suitable for various routes of administration including, but not limited to, orally, via injection or infusion, intraperitoneally, topically, nasally, ocularly, vaginally or rectally, in solid, semi-solid or liquid dosage forms as appropriate and in unit dosage forms suitable for effective administration or fixed dosages.

As used herein, physically acceptable fluid refers to any fluid or additive suitable for combination with a composition containing a hypocrellin derivative. Typically, these fluids are used as a diluent or carrier. Exemplary physiologically acceptable fluids include, but are not limited to, preservative solutions, saline solution, an isotonic (about 0.9%) saline solution, or about 5% albumin solution or suspension. It is intended that the present PLGA-nanoparticles are not to be limited by the type of physiologically acceptable fluid used.

The composition may also include pharmaceutically acceptable carriers. Pharmaceutically accepted carriers include but are not limited to saline, sterile water, phosphate-buffered saline, and the like. Other buffering agents, dispersing agents, and inert non-toxic substances suitable for delivery to a patient may be included in the compositions of the present embodiments. The compositions may be solutions, suspensions or any appropriate formulations suitable for administration, and are typically sterile and free of undesirable particulate matter. The compositions may be sterilized by conventional sterilization techniques.

In one aspect, a method for using the present biodegradable nanoparticle incorporating a photosensitizer and capable of being activated to generate singlet oxygen for anti-cell proliferation activity, is provided. The present method may comprise contacting a target tissue experiencing normal or abnormal cell proliferation such as, for example, a tumour or hair follicle, with the present nanoparticle, such that the present nanoparticle is internalized by the target tissue. The present method may further comprise using activation means to activate the present nanoparticle to generate cytotoxic singlet oxygen upon the exposure of the activation means. In one embodiment, the activation means may comprise light (e.g. photodynamic therapy (PDT) treatment). In another embodiment, the activation means may comprise hydrogen peroxide. It is known that administration of hydrogen peroxide may result in the production of oxygen and oxygen radicals, and may thus be used to activate the present nanoparticle. In a further embodiment, the activation means may comprise a combination of PDT treatment and hydrogen peroxide. It is contemplated that depending upon the particular photodynamic agent, photosensitizer or related compound, any activation means of producing and/or generating singlet oxygen may be utilized, such as, PDT treatment, hydrogen peroxide, ultrasound activation or a combination thereof.

As used herein, administering refers to any action that results in exposing or contacting hypocrellin B, or derivatives thereof, of the present embodiments with a predetermined cell, cells, or tissue, typically mammalian. As used herein, administering may be conducted in vivo, in vitro or ex vivo. For example, a composition may be administered by injection or via an endoscope. Administering also includes the direct application to cells of a composition according to the present embodiments. For example, during the course of surgery, tumour cells may be exposed. In accordance with an embodiment of the present PLGA-nanoparticles, these cells (or tumours) may be exposed directly to a composition of the present PLGA-nanoparticles, for example, by washing or irrigating the surgical site and/or the cells.

In another aspect, a method for delivering a photosensitizing compound capable of being activated to produce cytotoxic singlet oxygen at a target tissue is provided, the method comprising providing the present biodegradable polymeric nanoparticle comprising an inner core formed of hypocrellin B, or a derivative thereof, contacting the target tissue with an effective amount of the nanoparticle, wherein the nanoparticle is internalized by the tissue and is activated to release the hypocrellin B, or derivative thereof upon activation of the photosensitizing compound for the generation of cytotoxic singlet oxygen.

Exemplary embodiments of the present invention are described in the following Examples, which are set forth to aid in the understanding of the invention, and should not be construed to limit in any way the scope of the invention as defined in the claims which follow thereafter.

EXAMPLES

Example 1

Formation of PLGA-Nanoparticles

The present examples demonstrate the present PLGA-nanoparticles as a nanocarrier system for delivery of photosensitizing agents, and to compare the present PLGA-nanoparticles to known polyvinylpyrrolidone (PVP) nanoparticles.

The present photosensitizer-loaded PLGA-nanoparticles were prepared using a single-emulsion solvent evaporation technique involving both polymer and photosensitizer. Briefly, both the polymer and the photosensitizer were dissolved in an organic solvent, and the resulting organic solution was then emulsified (using a microtip probe sonicator) within the aqueous phase to form a water-in-oil (W/O) emulsion. The W/O emulsion was added to a vehicle to participate the nanoparticles, and the organic solvent was removed by evaporation to precipitate the nanoparticles. The resulting PLGA-nanoparticles can be collected by ultracentrifugation, washed with distilled water and freeze-dried. The nanoparticles may be stored at −20° C.

Figure 1:
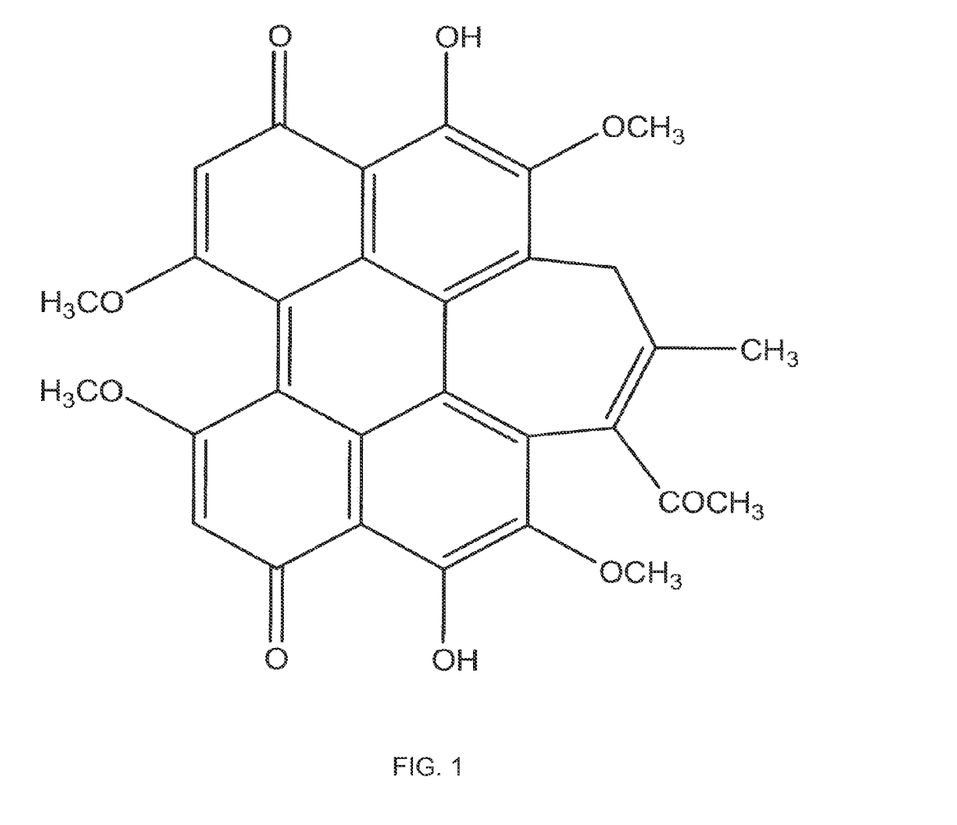
FIG. 1 shows the structure of hypocrellin B.

Different types of polymer, including a poly(lactic-co-glycolic acid) identified in terms of its terminal groups (e.g. COOH- or ester-terminated), can be associated to form the present PLGA-nanoparticles. The polymers may comprise an inherent viscosity ranging from 0.15-1.20 dL/g. Different types of photosensitizers, such as perylenequinone pigments hypocrellin B, or derivatives thereof, can be loaded into the present PLGA-nanoparticles. More specifically, the present PLGA-nanoparticles may comprise hypocrellin B, as depicted in FIG. 1, or modifications or derivatives thereof. As such, PLGA-nanoparticles comprising hypocrellin as a water-insoluble formulation for anti-tumour or hair removal clinical applications is provided.

Figure 2:
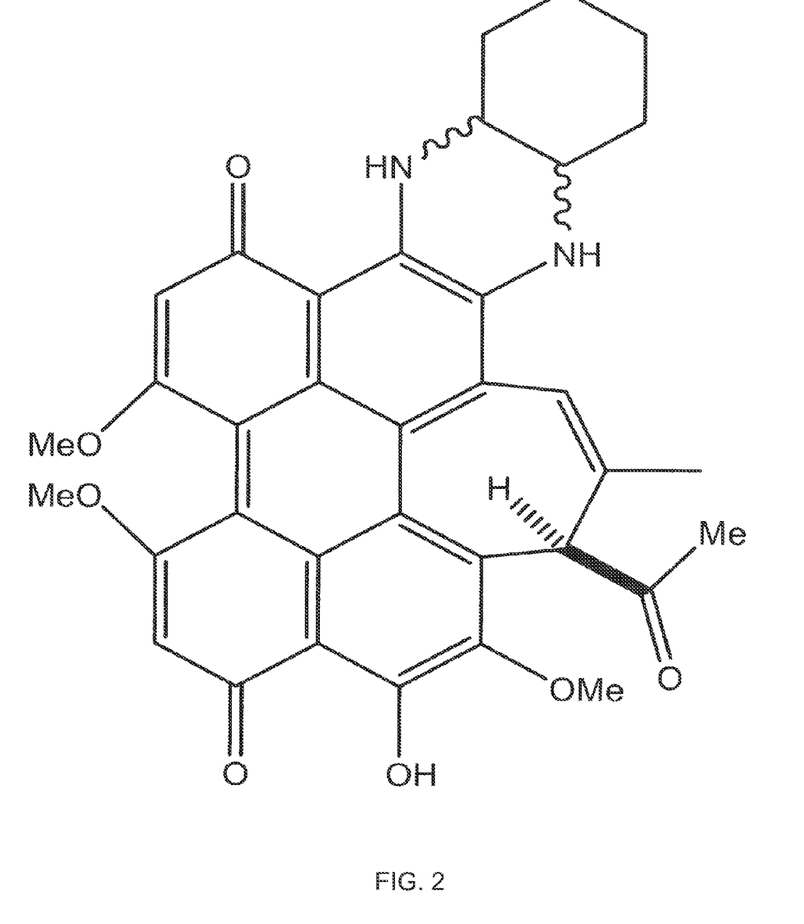
FIG. 2 shows the structure of a hypocrellin B derivative (SL052)

In one embodiment, the present nanoparticles may be formed using ester-terminated PLGA-nanoparticles containing the hypocrellin B or hypocrellin B derivative having the structure shown in FIG. 2 (hereinafter referred to as SL052; Quest PharmaTech Inc., Edmonton, Canada). For example, 100 mg of PLGA (ester-terminated (nominal) [PLGA], 50:50, inherent viscosity range: 0.26-0.54 dL/g in Hexafluoroisopropanol HFIP), (LACTEL absorbable polymers, DURECT Corporation, Pelham, Ala., USA), and 15 mg of SL052 were dissolved in chloroform (500 µl). The chloroform solution was emulsified in PVA (polyvinyl alcohol, 87-89% hydrolyzed, Mw 31000-50000, Sigma) solution in phosphate buffer saline (PBS; 2 mL of 5% w/v) using a probe sonicator. The emulsion was then added to 8 mL of 5% w/v PVA drop-wise, and the organic solvent was removed by evaporation. The resulting nanoparticles were then collected by, and washed with distilled water and then freeze-dried.

Figure 3:
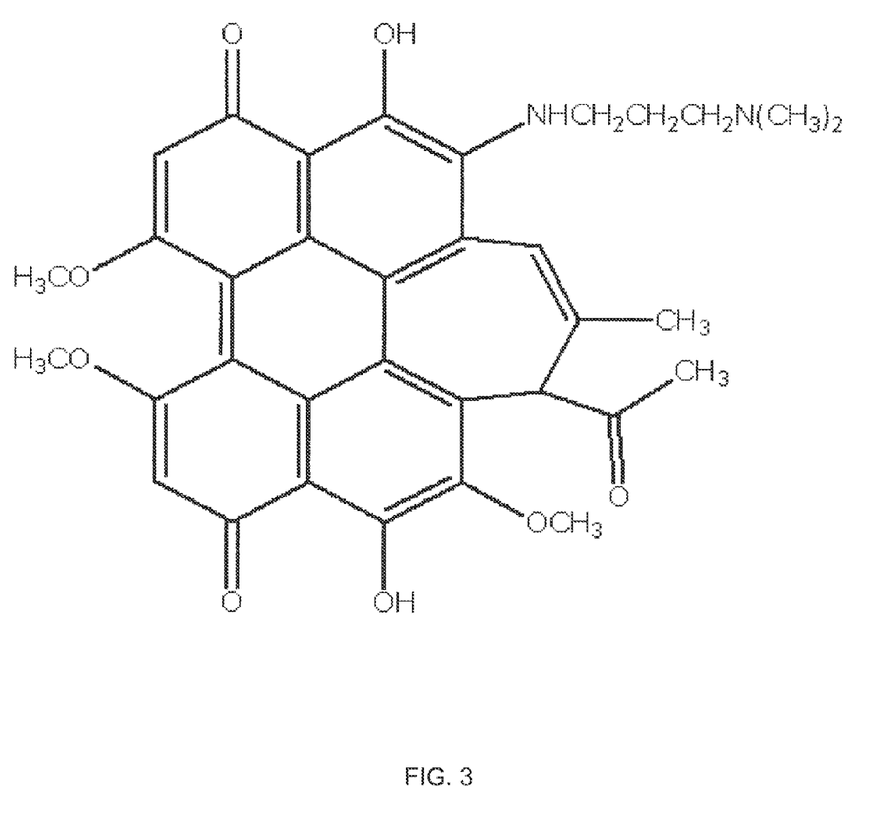
FIG. 3 shows the structure of a hypocrellin B derivative (SL017)

In another embodiment, the present nanoparticles may be formed using the COOH-terminated PLGA-nanoparticles containing the hypocrellin B derivative having the structure shown in FIG. 3 (hereinafter referred to as SL017; Quest PharmaTech Inc., Edmonton, Canada). For example, 100 mg of PLGA (COOH-terminated (nominal) [PLGA], 50:50, inherent viscosity range: 0.15-0.25 dL/g in HFIP, (LACTEL absorbable polymers, DURECT corporation, Pelham, Ala., USA) and 15 mg of SL017 were dissolved in methanol (1 mL). The resulting solution was emulsified in PVA (polyvinyl alcohol, 87-89% hydrolyzed, Mw 31000-50000, Sigma) solution in PBS (4 mL of 5% w/v) using a sonicator. This emulsion was then added drop-wise to 16 mL of distilled water and the organic solvent was removed by evaporation. The resulting nanoparticles were then collected by ultracentrifugation and washed with distilled water (at 35,000 g for 20 min, at 4° C.), and then freeze-dried.

Example 2

Structural Characterization of PLGA-Nanoparticles

Nanoparticle size and size distribution were determined using Dynamic Light Scattering. The analysis was performed at a scattering angle of 90° and at a temperature of 25° C. using sample appropriately diluted 100× with filtered distilled water (0.22 µm GV). UV-visible spectrophotometry was used to quantify the photosensitizers loaded in PLGA-nanoparticles. The absorbance was determined at a wavelength of 657 nm and the standard curve was plotted over a range of concentrations between 0 and 60 µg/ml of photosensitizer in DMSO. PLGA-nanoparticles loaded with photosensitizers were dissolved in DMSO and the absorbance were measured based on the standard curve. Empty PLGA-NPs were used as controls. The physicochemical characteristics for the present nanoparticles are summarized in Table 1. The parameters summarized were selected based upon their relevancy of providing an injectable and/or topical PLGA-nanoparticle entrapping a photosensitizer.

More specifically, the formulation for intravenous injection of the present SL052 PLGA nanoparticles, which showed the best results in-vivo found to have an average particle size of 337±55 nm and loading of 141±28 µg of SL052 per 1 mg of nanoparticles.

The present PLGA-nanoparticles incorporating SL017 with the maximum delivery to hair follicles represent an average size of the range 350±98 nm. These nanoparticles were able to encapsulate 95±24 µg of SL052 in 1 mg of nanoparticles.

Example 3

Determination of Uptake of PLGA-Nanoparticles

The uptake by tissue of the present nanoparticles was conducted in the following manner.

Example 3A

A topical formulation of 0.5% SL052 PLGA nanoparticles in pluronic lecithin organogel (PLO) gel was applied on a shaved area on the back of a Balb/c mouse. The formulation was incubated for 1 hour on the skin, and the excess drug was removed with a moistened tissue. A skin biopsy was removed from the treated area by punch biopsy, embedded in Optimal Cutting Temperature Compound (OCT, Sakura, Tokyo, Japan) and snap frozen.

Figure 4:
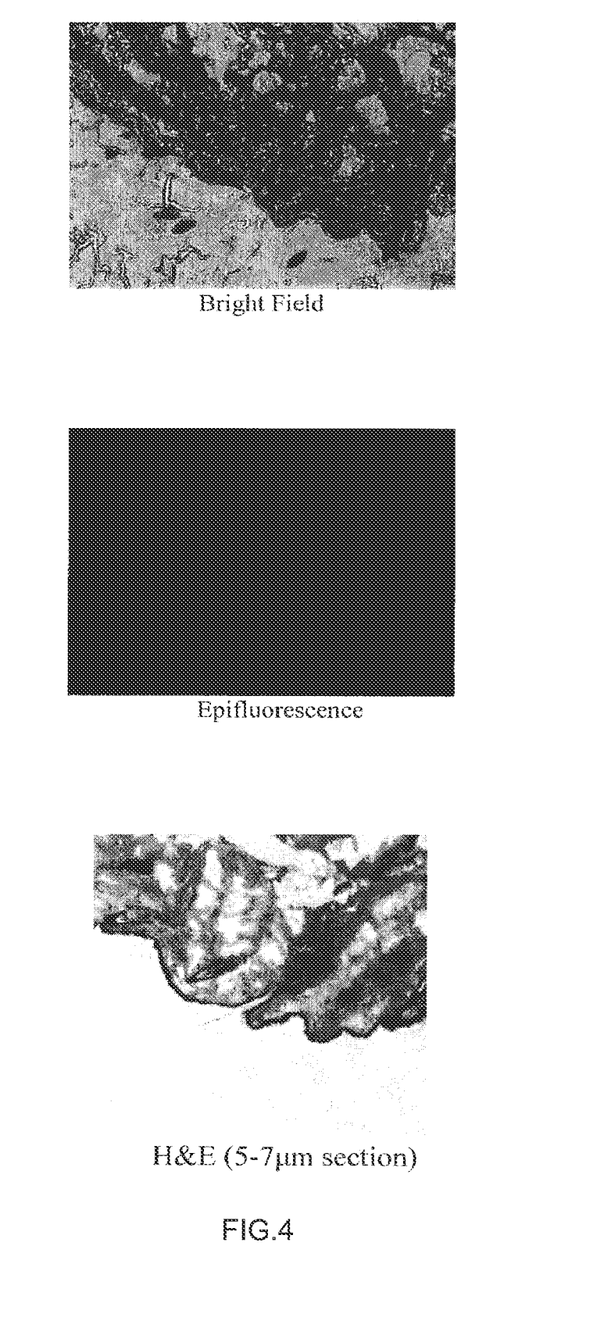
FIG. 4 shows the uptake of the present SL052 PLGA-nanoparticles by mouse skin.

Serial frozen sections of 7 µm were cut under minimal light exposure to prevent photobleaching. The first serial section was stained with Mayer's hematoxylin for 6 minutes (0.1% hematoxylin, 0.02% sodium iodate, 5% ammonium alum and 0.1% citric acid in distilled water), immersed for 10 seconds in acetic acid (2%), followed by 10 seconds in running water, 1 minute in 98.5% ethanol with 1.5% NH$_4$OH) and again running water for 10 seconds. The second unstained serial section was used to generate and record a fluorescence image of the sebaceous glands, epidermis and hair follicles (FIG. 4).

The fluorescence image demonstrates follicular penetration of the SL052 PLGA-nanoparticle in the mouse skin with the present nanoparticle formulation.

Example 3B

Figure 5A:
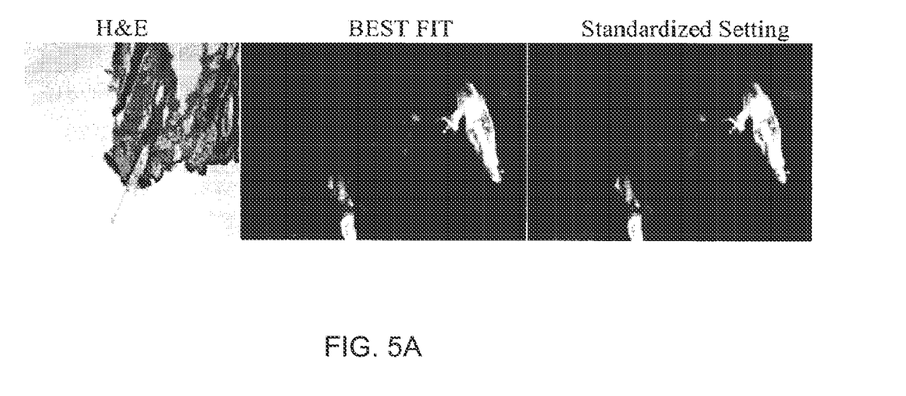
FIG. 5 shows the uptake of the present SL052 PLGA-nanoparticles by mouse skin.
Figure 5B:
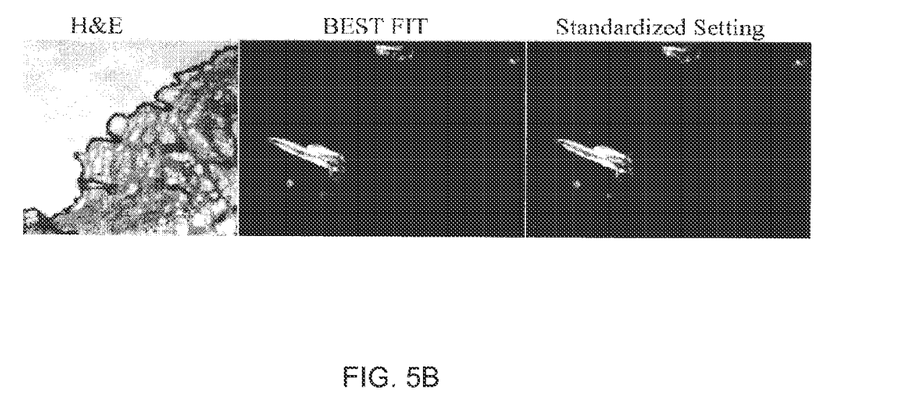
Figure 6:
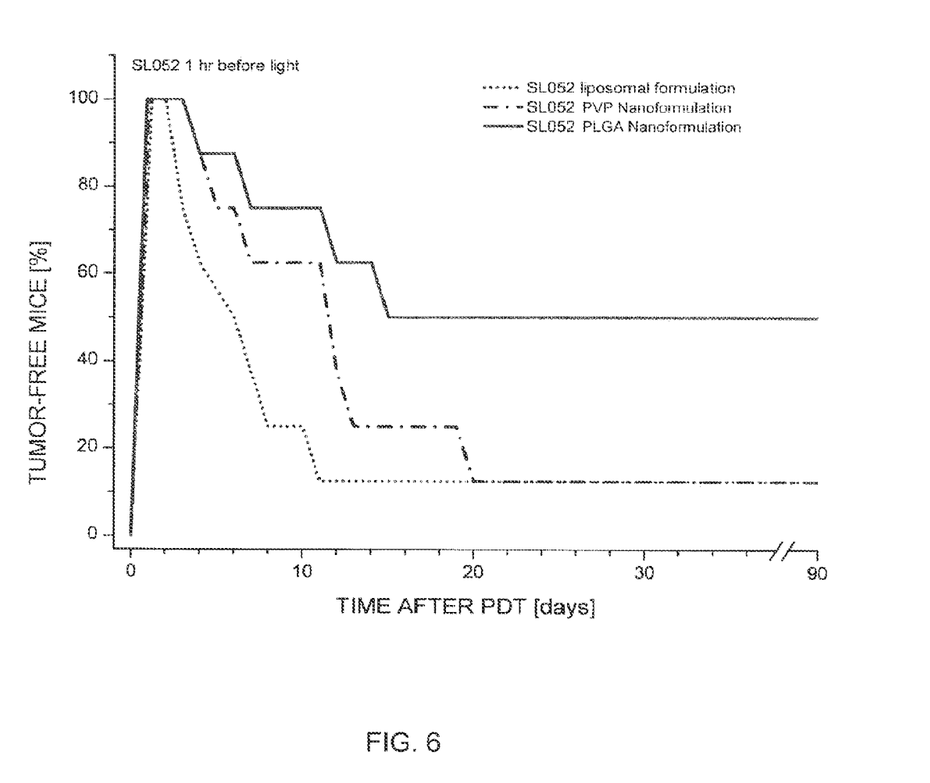
FIG. 6 shows the response of SCCVII tumours to PDT mediated by three different formulations of the present nanoparticles using a 1 hour interval between administration of the photosensitizer administration and light treatment; The results show that PLGA-nanoparticles deliver the photosensitizers to the tumours more significantly compared to other formulations.
Figure 7:
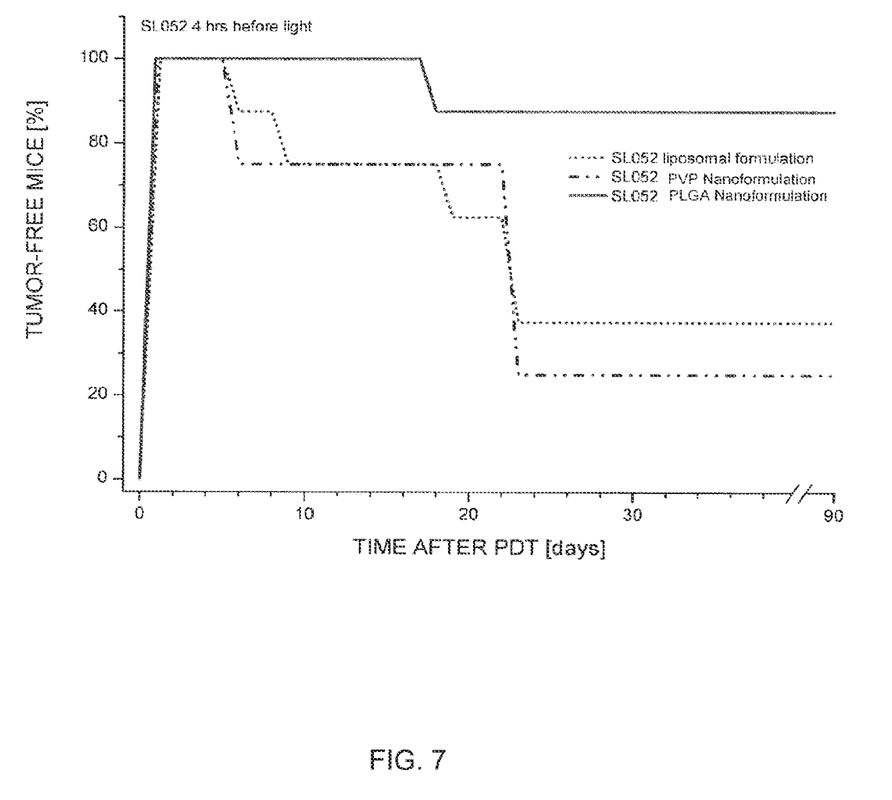
FIG. 7 shows the response of SCCVII tumours to PDT mediated by three different formulations of the present nanoparticles using a 4 hour interval between photosensitizer administration and light treatment.

A similar experiment was conducted using a 0.5% of the present SL052 PLGA-nanoparticle topical formulation in Natrosol. The formulation was incubated for 1 hour on the mouse skin, and the excess drug was removed with a moistened tissue. Skin biopsies were collected and embedded in OCT and snap frozen. The frozen sections of the biopsies were either H & E stained or read under a fluorescence microscope. The results are shown in FIGS. 5A and B.

Both of the foregoing Examples 3A and 3B showed increased penetration of the SL052 PLGA-nanoparticle formulation to deeper portions of the follicle.

Example 4

Determination of Photodynamic Activity

The photodynamic therapy (PDT) of two formulations of the present SL052 PLGA-nanoparticle, namely, PVP nanoparticle and a PLGA-nanoparticle were tested for the treatment of solid cancers. All testing in the present Example 4 was done to assess treatment of subcutaneous squamous cell carcinoma SCCVII tumours growing in the lower dorsal region of syngeneic C3H/HeN mice. Squamous cell carcinoma SCCVII is a well known model for human squamous cell carcinoma, particularly for head and neck cancer.

The different formulations, i.e. a PVP nanoparticle and a PLGA-nanoparticle were each injected intravenously at a dose of 4 mg/kg via the mouse tail vein.

In a first experiment, a one-hour interval passed before the tumour was treated with 200 J/cm2 of 665±10 nm light. After therapy, the mice were monitored for 90 days for signs of tumour growth, and those found without palpable tumours after that time interval was considered "cured". In a second experiment a longer four-hour interval passed between the dose administration and the light treatment. The results are summarized in FIGS. 6 and 7.

The results for the 1-hour photo sensitizer-light interval (FIG. 6) show that 50% tumour cures were attained with the present PLGA-nanoparticle encapsulating the SL052 photosensitizer, while only 12.5% tumour cures were obtained with the other two formulations. The increase in the therapeutic efficacy with the present PLGA-nanoparticle compared to the two other formulations was statistically significant ($p<0.05$). There was no significant difference, however, in the therapeutic efficacy of the PVP-nanoparticle encapsulating the photosensitizer SL052 compared to the standard liposomal SL052 formulation ($p<0.05$).

Example 5

In Vitro Activation of SL052 by Hydrogen Peroxide

The cytotoxic activity of SL052 after activation with hydrogen peroxide was studied using WST-1 dye as an indicator of cell survival. The reduction of WST-1 by viable cells produces a soluble formazan salt, which can be quantified spectrophotometrically at 450 nm. BT549, a human breast carcinoma cell-line is cultured in a 96 well plate. SL052 is added to the wells at 0, 1, 5 and 10 μM drug concentrations. After a 3 hour incubation period, hydrogen peroxide at 1, 2.5, 5 or 10 μM final concentration is added to the wells and allowed to incubate for a further 30 minutes. The treated plates are then washed and the WST-1 dye added to the treated wells and incubated overnight. The decrease in absorbance at 450 nm in the treated wells represented the degree of growth inhibition after the treatment. The results are summarized in FIG. 8.

Figure 8:
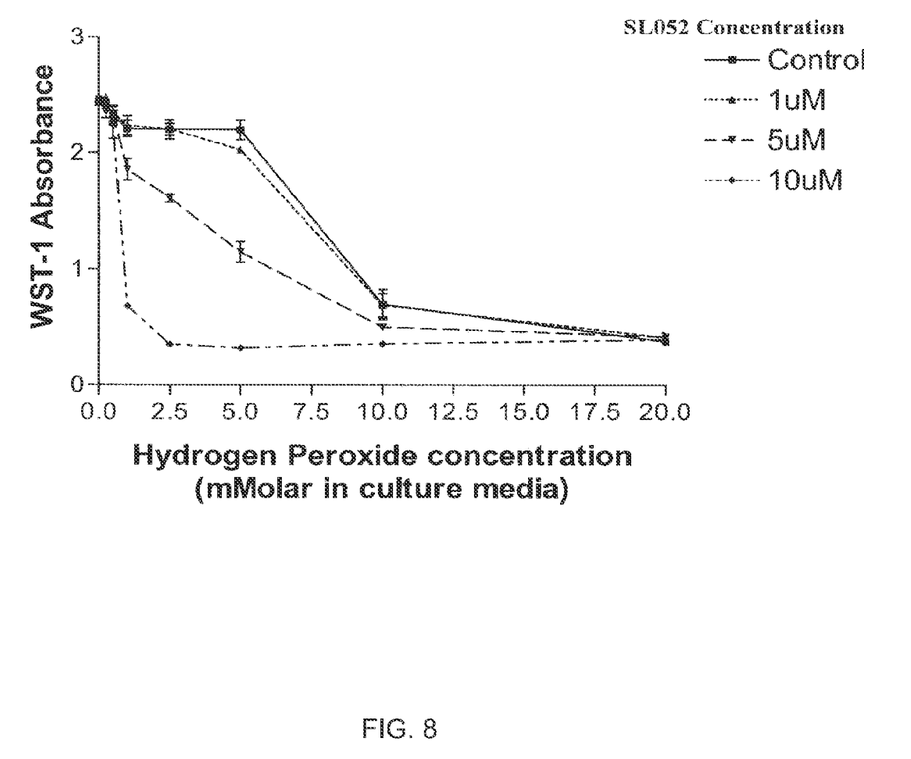
FIG. 8 shows the effect of hydrogen peroxide activation of SL052 on BT-549 cells; The cell killing effect of activated SL052 is monitored by a WST-1 cell proliferation reagent. The results demonstrate the activation of SL052 at a concentration of 5 to 10 μM by the addition of hydrogen peroxide.

The results provide the unexpected and unpredicted result that the present polymeric nanoparticle encapsulating the photodynamic agent SL052 can be activated by the addition of hydrogen peroxide to effect cell-killing in vitro. A dose response is seen with regard to the amount of SL052 and the concentration of hydrogen peroxide (below 10 μM).

While not completely understood, it is contemplated that the structural nature of the present polymeric-nanoparticles encapsulating the photodynamic agents SL052 and SL017, and in particular the location of the double bonds within the SL052 and SL017 structures, may facilitate activation by hydrogen peroxide and particularly low-dose hydrogen peroxide.

Example 6

In Vivo Activity of SL052 on EMT-6 Implanted Tumours by Activation with Hydrogen Peroxide The cytotoxic activity of hydrogen peroxide activated SL052 was investigated using an EMT-6 tumour model in Balb/c mice. The EMT-6 tumor was implanted bilaterally and subcutaneously in the flank and allowed to grow until it reached approximately 3 to 5 mm diameter in size on both sides of the mouse.

SL052 was dissolved in pure DMSO to give a final concentration of 5 mg/mL. The mice were anaesthetized with Sodium Pentobarbital at 12 mg/mL by intraperitoneal injection. Once the mice were sedated they were shaved over each tumour, and 25 μL of SL052/DMSO was topically applied directly to the skin over the tumour with gentle massage to facilitate contact. The tumour on one flank was treated with hydrogen peroxide gel at a concentration of 10% hydrogen peroxide, and incubated for a predetermined time interval of 30 or 60 minutes. The tumour on the other flank was treated with 100 Joules/cm$^2$ of 635 nm light for 30 minutes post topical application.

The mice were observed daily and tumour measurements were taken by calliper measurement to determine treatment efficacy. The end points were either when the tumour reached 4× the initial treatment volume, or when the tumour was no longer palpable and was considered "cured".

Two groups of mice treated with SL052 only (see FIG. 9, "Drug Only") or with hydrogen peroxide only (see FIG. 9, "HP only") served as controls.

Figure 9:
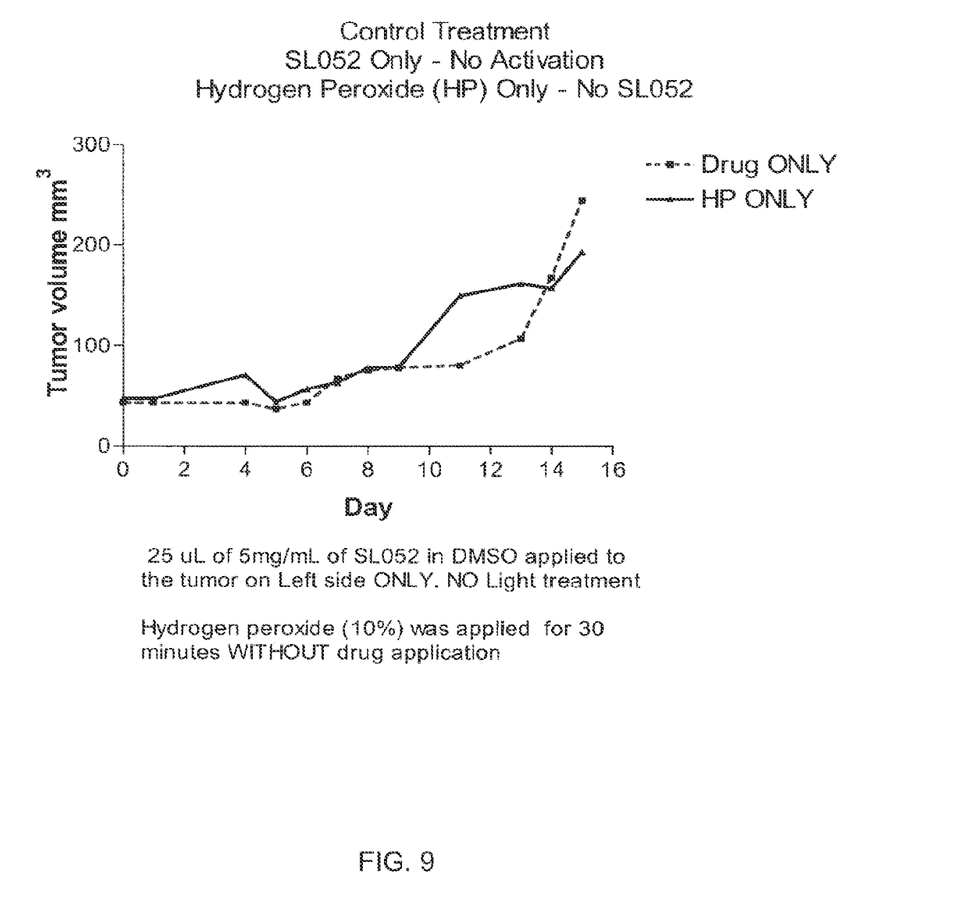
FIG. 9 shows the growth of EMT-6 Tumours with SL052 alone without activation, or with hydrogen peroxide only (no SL052)
Figure 10:
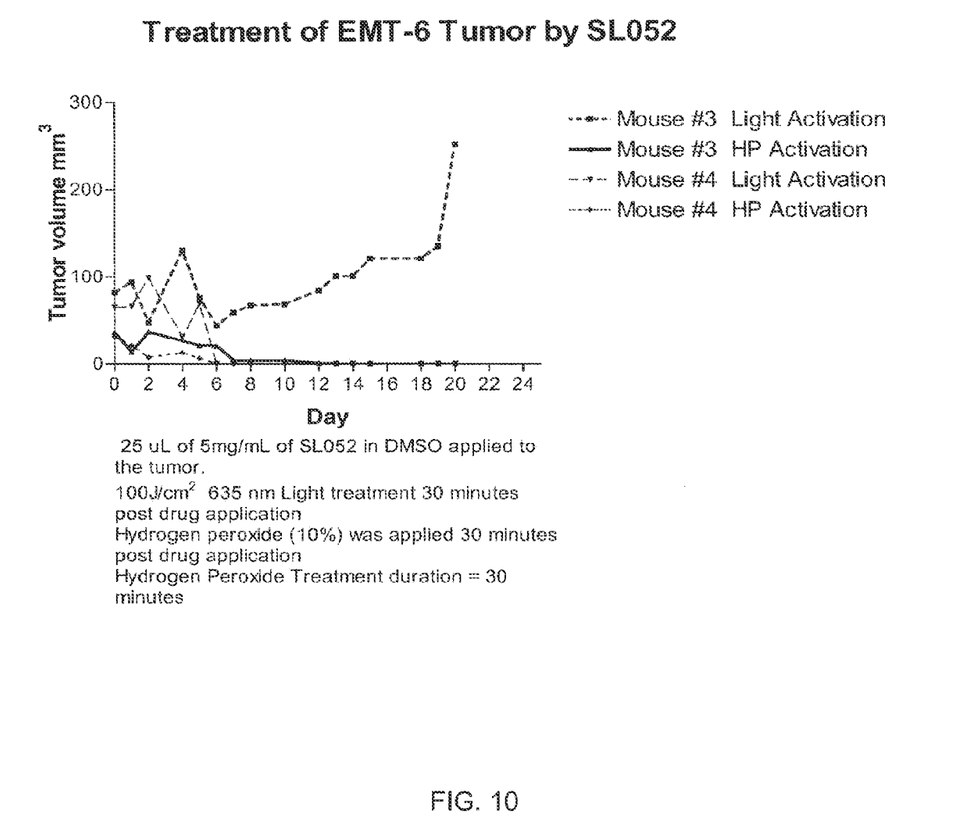
FIG. 10 shows the treatment of EMT-6 Tumours with SL052 following 30 minutes of hydrogen peroxide treatment compared with light treatment.

Neither control group exhibited any tumour control activity. The results from the hydrogen peroxide and light activated treatment are shown in FIG. 10 (30 minutes hydrogen peroxide treatment) and FIG. 11 (60 minutes hydrogen peroxide treatment).

Figure 11:
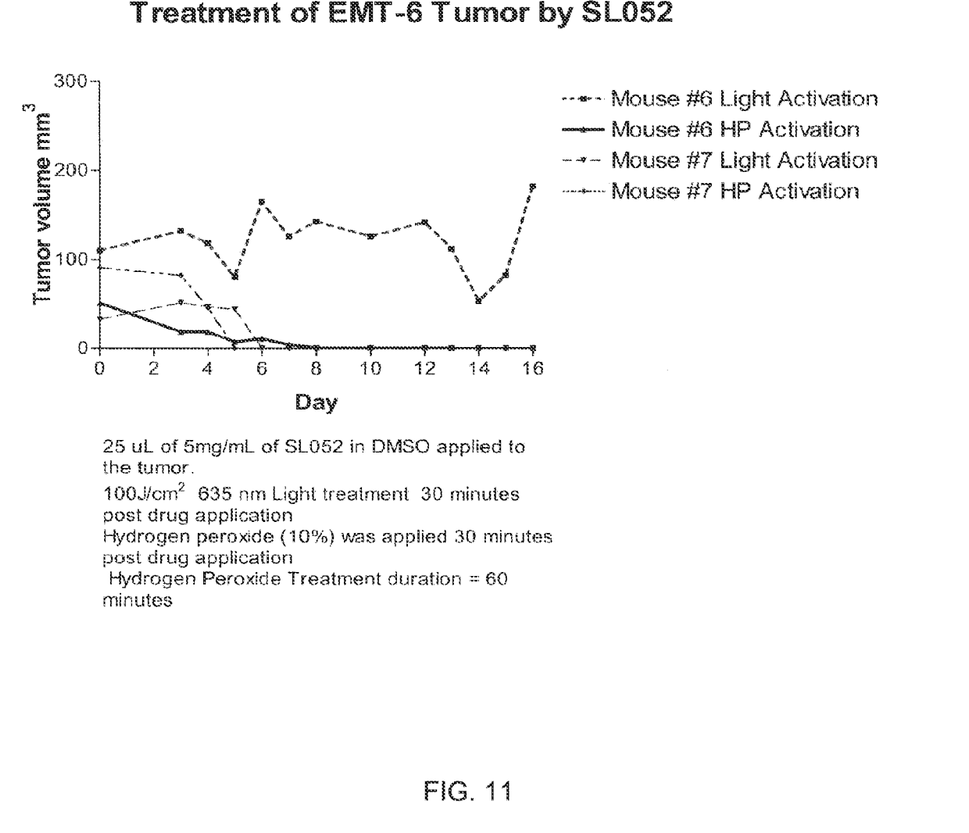
FIG. 11 shows the treatment of EMT-6 Tumours with SL052 following 60 minutes of hydrogen peroxide treatment compared with light treatment; and
Table 1 shows the formulation parameters and physicochemical properties of the present nanoparticles.

The results demonstrate that the present polymeric nanoparticle encapsulating the photodynamic agent having the structure of SL052 can be activated by the addition of hydrogen peroxide to effect cell-killing in vivo. This cytotoxicity results in significant tumor growth delay.

Example 7

Use of SL052 in the Treatment of Actinic Keratoses

A topical formulation of 0.5% SL052 PLGA nanoparticles in Natrosol gel was used for the treatment of actinic keratoses (AK) lesions on patients using hydrogen peroxide for activation of SL052. The patients were instructed to clean the AK lesions twice a day with soap and water, followed by the application of the SL052 PLGA gel directly on the lesions. The formulation is massaged into the area with a gentle circular motion for a few minutes. After the product has dried, one to two drops of 12% hydrogen peroxide solution is applied to the treated area. The regimen is repeated daily for 21 days. One patient receiving the treatment showed visible improvement in the treated areas.

What is claimed:

1. A method for providing singlet oxygen for anti-cell proliferation activity topically to target tissue comprising the steps of:
    a) contacting said tissue with an effective amount of a biodegradable polymeric nanoparticle comprising:
    an inner core formed of a photodynamic agent selected from the group consisting of or a combination thereof, and
    a polymer selected from the group consisting of polyglycolic acid, polylactic acid or a poly(lactic-co-glycolic acid); and
    b) contacting said tissue with hydrogen peroxide.

2. The method of claim 1, wherein the polymer comprises poly(lactic-co-glycolic acid) having an ester-terminus.

3. The method of claim 1, wherein the polymer comprises poly(lactic-co-glycolic acid) having a free carboxylic acid terminus.

4. The method of claim 1, wherein the nanoparticles have an average diameter that is approximately 100-400 nm.

5. The method of claim 4, wherein the nanoparticles have an average diameter of approximately 200 nm.

* * * * *